United States Patent [19]

Hjort

[11] 4,084,583
[45] Apr. 18, 1978

[54] METHOD AND APPARATUS FOR MEASURING THE BIOELECTRICAL ACTIVITY UNDER AN ELECTRODE RESTING ON A PATIENT

[75] Inventor: Bo Hjort, Sollentuna, Sweden

[73] Assignee: Siemens Aktiengesellschaft, Berlin & Munich, Germany

[21] Appl. No.: 674,607

[22] Filed: Apr. 7, 1976

[30] Foreign Application Priority Data

Apr. 24, 1975 Germany .............................. 2518269

[51] Int. Cl.² .................................................. A61B 5/04
[52] U.S. Cl. ........................... 128/2.06 R; 128/2.06 E; 128/2.1 R; 128/2.1 E; 128/DIG. 4
[58] Field of Search ............... 128/2.06 R, 2.06 B, 128/2.06 E, 2.06 G, 2.06 V, 2.1 B, 2.1 M, 2.1 R, 2.1 Z, 2.1 E, DIG. 4

[56] References Cited

U.S. PATENT DOCUMENTS 2,549,836  4/1951   McIntyre et al. ................. 128/2.1 B
3,848,582  11/1974  Milani et al. ..................... 128/2.06 E

FOREIGN PATENT DOCUMENTS 739,227   7/1966   Canada ............................. 128/2.06 B
1,355,600 2/1964   France ............................. 128/2.06 E

OTHER PUBLICATIONS

Takagi et al., "The Electrodes-Triangle", Amer. Heart J., Sept. 1970, pp. 427–428.

Primary Examiner—Robert W. Michell
Assistant Examiner—Lee S. Cohen
Attorney, Agent, or Firm—Hill, Gross, Simpson, Van Santen, Steadman, Chiara & Simpson

[57] ABSTRACT

Method and apparatus for measuring the bioelectrical activity of a patient, wherein a signal electrode is placed on a patient and a plurality of auxiliary electrodes are placed adjacent the signal electrode. The auxiliary electrodes are connected by a resistor network to provide a mean potential value and the difference between the mean potential value and the potential of the signal electrode is determined and fed to a recorder which indicates this difference value as indicative of the bioelectric activity under and within proximity of the signal electrode. The auxiliary electrodes can be arranged at the corners of a polygon with the signal electrode disposed in the center of the polygon. The entire assembly of electrodes can be mounted on a support device of insulating material.

5 Claims, 14 Drawing Figures

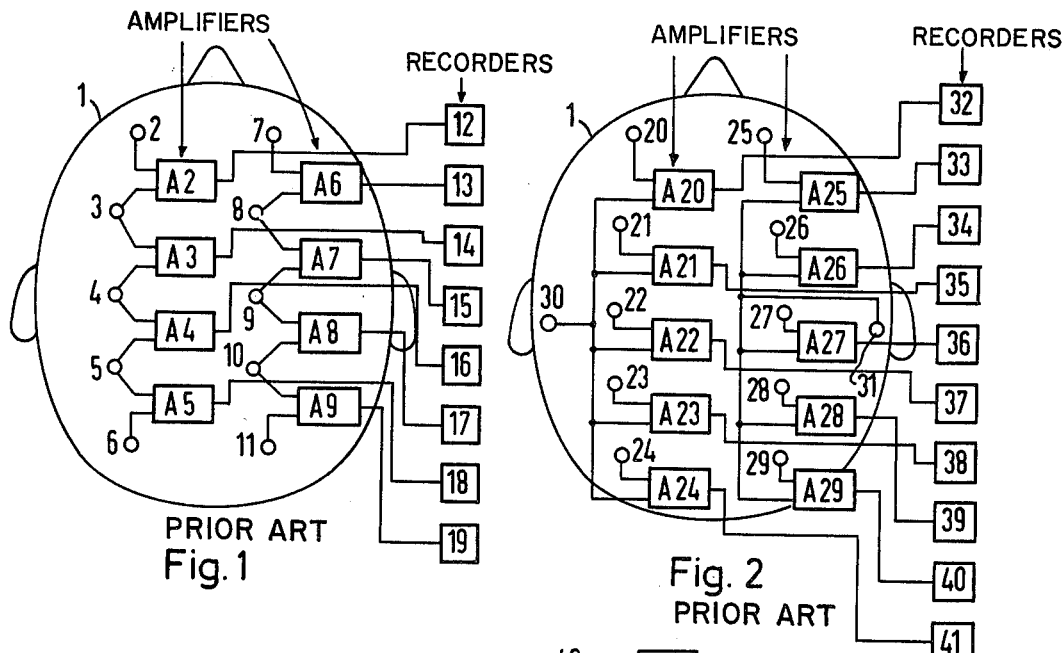
Fig. 1 PRIOR ART
Fig. 2 PRIOR ART
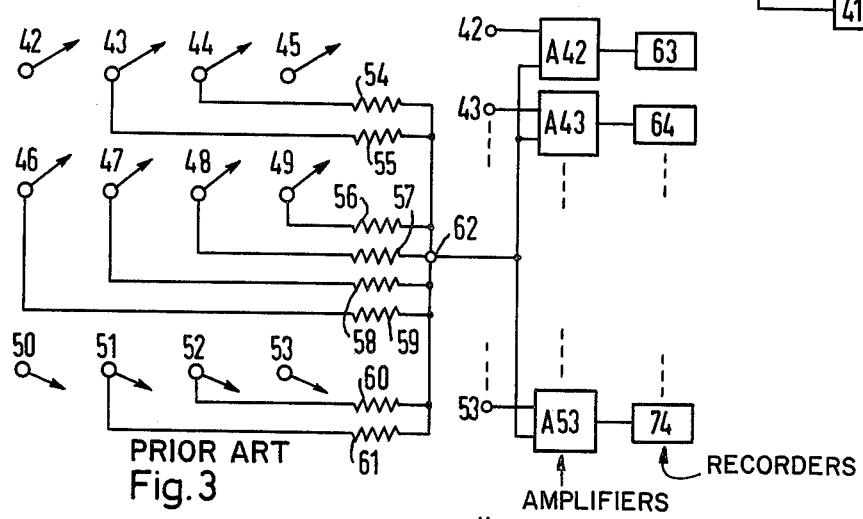
Fig. 3 PRIOR ART
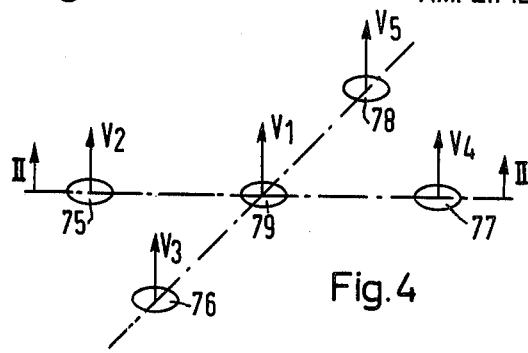
Fig. 4

AMPLIFIER    RECODER

AMPLIFIERS    RECORDERS

METHOD AND APPARATUS FOR MEASURING THE BIOELECTRICAL ACTIVITY UNDER AN ELECTRODE RESTING ON A PATIENT

FIELD OF THE INVENTION

The present invention relates to a method for measuring the bioelectric activity which occurs under a measuring electrode (signal electrode) attached to or resting on a patient, in which method a plurality of auxiliary electrodes attached to the patient are employed whose potentials produce a mean potential value, and wherein the difference between said mean potential value and the potential of the signal electrode is measured and supplied, for example, to a device for recording the measured value.

BACKGROUND OF THE INVENTION

A known method of the above type is employed, for example, for the purpose of measuring signals of the central nerve system. Such a measuring process is carried out either by means of a number of electrodes which are arranged on the skull of the patient in a pattern conforming to internationally established standards (electroencephalography — EEG), or by using a number of electrodes which are applied to the exposed cerebral cortex, or to the cerebral meninger (electrocortigraphy — ECOG). The electrical activity of the nerve cells and the surrounding medium is picked up under the electrodes in the form of respective potential variations. The electrodes in both methods, are associated with after-connected amplifiers and recording or registering devices.

The measuring methods may be divided into bipolar and unipolar measuring processes. A bipolar measuring method comprises feeding the potential differences to the amplifier inputs which are engaged in pairs between the electrodes. In the unipolar measuring method, the potential differences are picked up between a number of electrodes and a reference point which in each case is common for said electrodes. Said reference point may be a physical electrode or, for example, the center point of a resistor network which is connected with the same resistance value to all electrodes, or optionally with the exclusion of those electrodes whose signals, on the basis of past experience, are known to adversely affect the results of the measurement because they are caused, for example, by the activity of muscles. The shortcomings of said two measuring methods are that each measured potential is the difference between two electrode potentials, which means that a selective pickup of each local change in electrode potential does not take place. Accordingly, it is not possible to exactly locate the cerebral bioelectric activity.

Furthermore, both these measuring methods are impaired by an instability factor caused by the fact that the electrode potentials are composed of the electrical activity both of the cerebral tissue disposed directly beneath the electrode and the electrical activity of an adjacent ring which is passed laterally on the skull.

The above-mentioned known measuring methods are described in greater detail later with reference to FIGS. 1 to 3.

SUMMARY OF THE INVENTION

It is an object of the present invention to provide a measuring method of the afore-stated type which will make it possible in a simple manner to engage and pick up the electrical activity present locally beneath a measuring electrode.

According to the present invention, this object is achieved by limiting the use of auxiliary electrodes exclusively to electrodes which are disposed adjacent the signal electrode.

An advantageous arrangement for carrying out the measuring method comprises supporting the signal electrode and the auxiliary electrodes on a holder composed of insulating material.

Additional advantages and details of the present invention will become apparent from the description of embodiments thereof with reference to the attached drawings.

BRIEF DESCRIPTION OF THE DRAWINGS

FIGS. 1 to 3 are schematic views of conventional measuring methods;

FIG. 4 shows an electrode arrangement illustrating the method according to the present invention;

DETAILED DESCRIPTION

Figure 5:
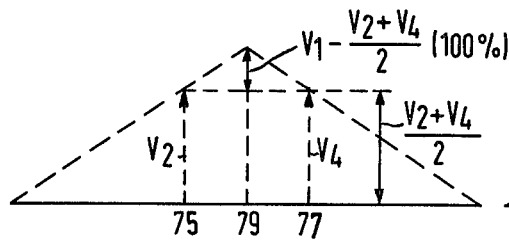
FIGS. 5 to 8 illustrate the potential patterns or paths as taken along line II—II in FIG. 4.
Figure 6:
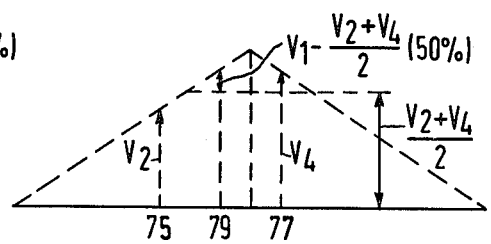

FIG. 1 shows a bipolar measuring method. Therein, the skull of a patient 1 carries ten electrodes 2 to 11 placed symmetrically thereon. The amplifier inputs of amplifiers A2 to A9 associated with electrodes 2 to 11 receive in pairs potential differences existing in each case between the associated electrodes. The voltage differences are supplied, after amplification, to recording devices 12 to 19 which, for example, may be ink jet recorders according to German Pat. Spec. No. 821,065.

FIG. 2 shows a unipolar measuring method. Therein, 12 electrodes 20 to 31 are arranged symmetrically on the skull of patient 1. The electrodes 20 to 29 are respectively connected to one input of amplifiers A20 to A29. To the second inputs of amplifiers A20 to A24, there is connected electrode 30, and electrode 31 is connected to the second inputs of amplifiers A25 to A29. This means that in this case, electrodes 20 to 24 supply five potentials to amplifiers A20 to A24, with the potential of electrode 30 being the common reference potential, and in the same manner five potentials are supplied by electrodes 25 to 29 to amplifiers A25 to A29, with the potential of electrode 31 being the common reference potential. The amplifiers A20 to A29 conduct the difference between the potentials of electrodes 20 to 24 and the potential of reference electrode 30, or respectively between the potentials of electrodes 25 to 29 and the potential of reference electrode 31, to ink jet recorders 32 to 41.

FIG. 3 illustrates a further unipolar measuring method wherein twelve electrodes 42 to 53 are symmetrically arranged and connected in each case to one input of amplifiers A42 to A53. To eight electrodes 43, 44, 46, 47, 48, 49, 51 and 52, there are connected equal resistors 54 to 61, one of the ends of said resistors being connected to a common center point 62 (reference point). All 12 amplifiers A42 to A53 are connected at their second inputs to point 62. With respect to the four electrodes 42, 45, 50 and 53, it is assumed that these electrodes will pick up potentials of a non-cerebral type (for example, caused by muscle activity) to an extent exceeding the pick up of such non-cerebral potentials of the other electrodes, so that the former electrodes (42, 45, 50, 53) are not connected to the resistor star. Each of the amplifiers A42 to A53 measures the difference between an electrode potential and a mean value potential. The difference voltages are supplied to ink jet recorders 63 to 74 for recording these values. The mean value potential amounts to ⅛th of the sum of the electrode potentials beneath electrodes 43, 44, 46, to 49, 51 and 52. If the mean value potential at reference point 62 is equal or larger than the potential of the individual electrode, the individual potentials of the electrodes cannot be picked up. This may be the case if some of the electrode potentials are substantially higher than others, because the result at point 62 will then be determined substantially by these substantially higher electrode potentials.

In FIG. 4, the actual measuring electrode (signal electrode) is designated by reference number 79, the potential of which electrode is to be measured, whereas the reference numerals 75 to 78 designate auxiliary electrodes. Said auxiliary electrodes are disposed in such a manner that they form a regular polygon (a square in the example of the figure), with the signal electrode 79 being disposed in the center of the polygon. Beneath electrodes 75 to 79, there are present the potentials $V_1$ to $V_5$. According to the present invention, the following voltage value is formed:

$$V_1 - \frac{V_2 + V_3 + V_4 + V_5}{4}$$

This voltage is strongly influenced by the potentials occurring within the surface area limited by auxiliary electrodes 75, 76, 77, 78.

Figure 7:
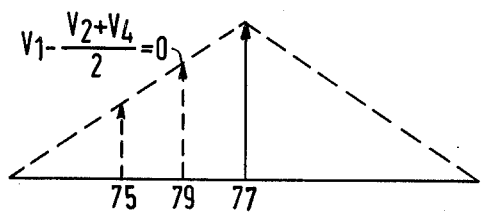
Figure 8:
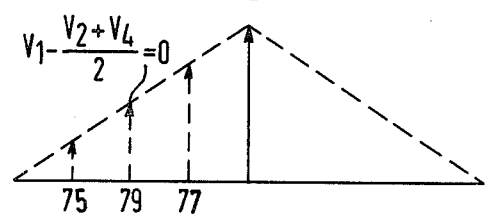

In order to permit an understanding of the spatial limitation of the sensitivity distribution, attention is directed to FIGS. 5 to 8 which show by way of example different potential values below line II—II in FIG. 4. In order to simplify calculations, it is assumed that the potential declines in accordance with a linear function in the plane extending through electrodes 75, 77, 79, and vertically relative to the surface of the body of the patient. The bias or difference in potential formed according to the invention, namely $$V_1 - \frac{V_2 + V_4}{2}$$

is the highest (100%) if the center of the potential field (potential center) is located in said plane precisely under signal electrode 79 (FIG. 5). The voltage will be reduced to half that value (50%) if the potential center is located in the middle between signal electrode 79 and auxiliary electrode 77 (FIG. 6), and it will be zero if the potential center is located under an auxiliary electrode or outside of the polygon determined by the auxiliary electrodes (FIGS. 7 and 8). In reality, the potential declines along the skull more in accordance with an exponential function whose exponent slightly influences the exactness of the determination of the desired potential; however, this has no decisive bearing on the essence of the present invention.

Figure 9:
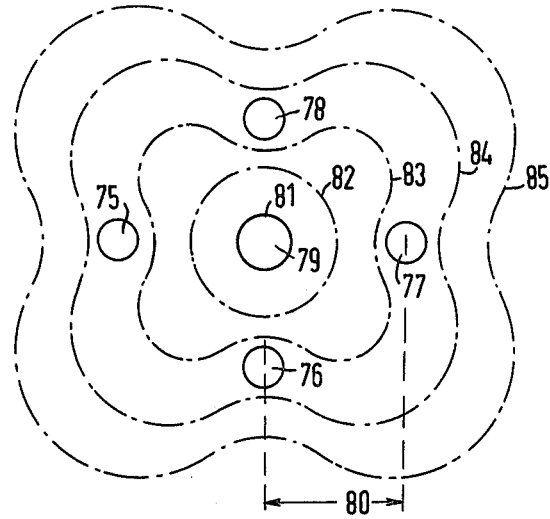
FIG. 9 is a top plan view of the distribution of sensitivity in the electrode arrangement according to FIG. 4.

In FIG. 9, wherein 79 is the signal electrode and 75 to 78 designate the auxiliary electrodes, the assumption is made that the exponent of attenuation of the bioelectric potential, in terms of its magnitude, is such that the half-value spacing is equal to the spacing 80 between signal electrode 79 and auxiliary electrode 77. Half-value spacing refers, in this instance, to the spacing between two points which are radially removed from the center of the potential, with the potential declining to one-half its value between said two points. With different half-value spacings, one of the level lines described below will change; however, the principle is maintained. Reference numerals 81 to 85 designate contour lines having the following significance, or meaning: if the potential center which is to be measured bioelectrically is located on contour line 81, i.e., exactly under signal electrode 79, the bias voltage $$V_1 - \frac{V_2 + V_3 + V_4 + V_5}{4}$$

is attributed the summation value of 100%.

If the center of the potential is located on contour line 82, the bias voltage has the summation value of 50%, and if the center of the potential is located on contour line 84, the bias or difference in potential is zero and remains within the proximity of zero if the center of the potential is located further outside of contour line 84. For example, the bias is attributed the sum −1% for a potential center located on contour line 85.

This means that the bias voltage according to the present invention will indicate with a high degree of spatial exactness the bioelectrical activity prevailing within the polygon formed by the auxiliary electrodes. The bias voltage, which is representative of the bioelectrical activity present under and within the proximity of the signal electrode, increases with the number of auxiliary electrodes used in the system. The embodiment shows four symmetrically disposed auxiliary electrodes 75 to 78; however, three, five or more electrodes may be used. It is not necessary to arrange the auxiliary electrodes symmetrically relative to the signal electrode. Furthermore, errors of measurement occurring in connection with auxiliary electrodes arranged in an unsymmetrical layout or pattern may be eliminated if the auxiliary electrodes are connected to the neutral point by way of resistors with values depending on the spacing provided in each case between the auxiliary electrode and the signal electrode.

Figure 10:
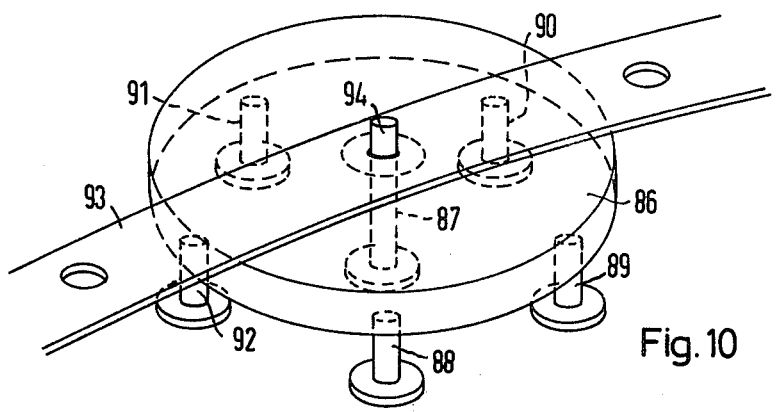
FIG. 10 shows an electrode arrangement for carrying out the measuring method according to the invention.
Figure 11:
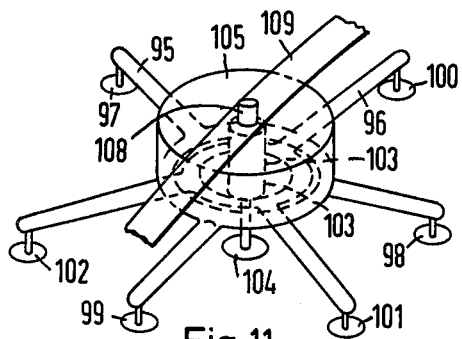
FIG. 11 shows a further electrode arrangement for the measuring method according to the present invention.
Figure 12:
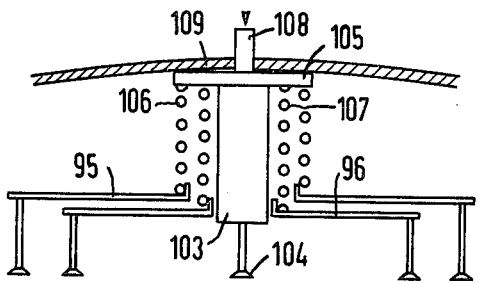
FIG. 12 illustrates a side view of the arrangement shown in FIG. 11.

FIGS. 10 to 12 show electrode-support devices in which the electrodes are mounted in such a way that a bias voltage is obtained in accordance with the above-described measuring method.

The electrode mounting device in FIG. 10 comprises a disk 86 composed of insulating material; the signal electrode 87 is secured in the center of said disk. The auxiliary electrodes 88 to 92 are disposed at the periphery of said mounting device and form the corners of a regular polygon (pentagon). All electrodes are secured or mounted vertically on their support surfaces by means of known elastic means which are not shown in the figure. An elastic band 93 is pushed onto or over a pin 94 and presses the electrode-support device against the surface of application on the patient.

FIGS. 11 and 12 illustrate an electrode support device of insulating material which is formed by two triangles 95, 96, which each support three auxiliary electrodes 97 to 99, and 100 to 102. A shaft 103 projects through the common center of said triangles 95, 96, and carries a signal electrode 104 which is attached to the downwardly facing end of said shaft. The other end of face side of shaft 103 supports a disk 105 whose diameter is larger than the diameter of said shaft. Between disk 105 and triangles 95 and 96, there are arranged coil springs 106, 107, in such a way that the triangles 95 and 96 are rendered elastic independently of each other. Disk 105 is further provided with an upwardly extending pin 108 onto which an elastic band 109 is placed for the purpose of pressing the electrode-support device against the surface of application. When said elastic band 109 urges the signal electrode 104 against the surface of application, electrodes 97 to 102 of the two triangles receive a certain pressure of application which is dependent on coil springs 106 and 107.

The electrode-support devices described above are small in size; the spacing between the signal electrode and the auxiliary electrodes is about 1 to 2 cm, so that a number of signal electrodes together with a respective number of auxiliary electrodes may be applied which will conform to the number of signal electrodes applied customarily in connection with known measuring methods. The electrode-support device shown in FIGS. 11 and 12 comprise a particularly advantageous construction comprising two adjacent electrode holders which may be combined by inserting one into the other.

Figure 13:
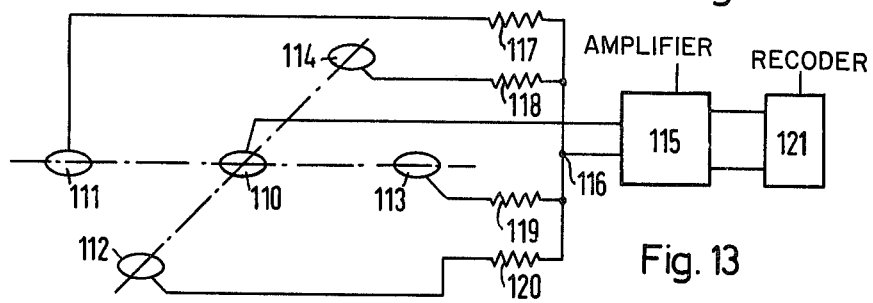
FIG. 13 is a circuit diagram illustrating the measuring method according to the invention.

FIG. 13 illustrates the manner in which the differance voltage is formed which is characteristic of the present invention. Namely in the aforedescribed electrode arrangements, the difference voltage is formed as the difference between the potential of signal electrode 110, which potential is supplied to the input of differential amplifier 115, and the mean value of the potentials of auxiliary electrodes 111 to 114, said mean value being received at reference point 116 and supplied to the second input of said differential amplifier 115.

Between reference point 116 and the auxiliary electrodes 111 to 114, there are disposed equal resistors 117 to 120 because the spacing between signal electrode 110 and auxiliary electrodes 11 to 114 is also equal in such case. The difference voltage between the potential of signal electrode 110 and the potential of point 116 is amplified in differential amplifier 115 and further supplied to a recording means 121 for registration.

Figure 14:
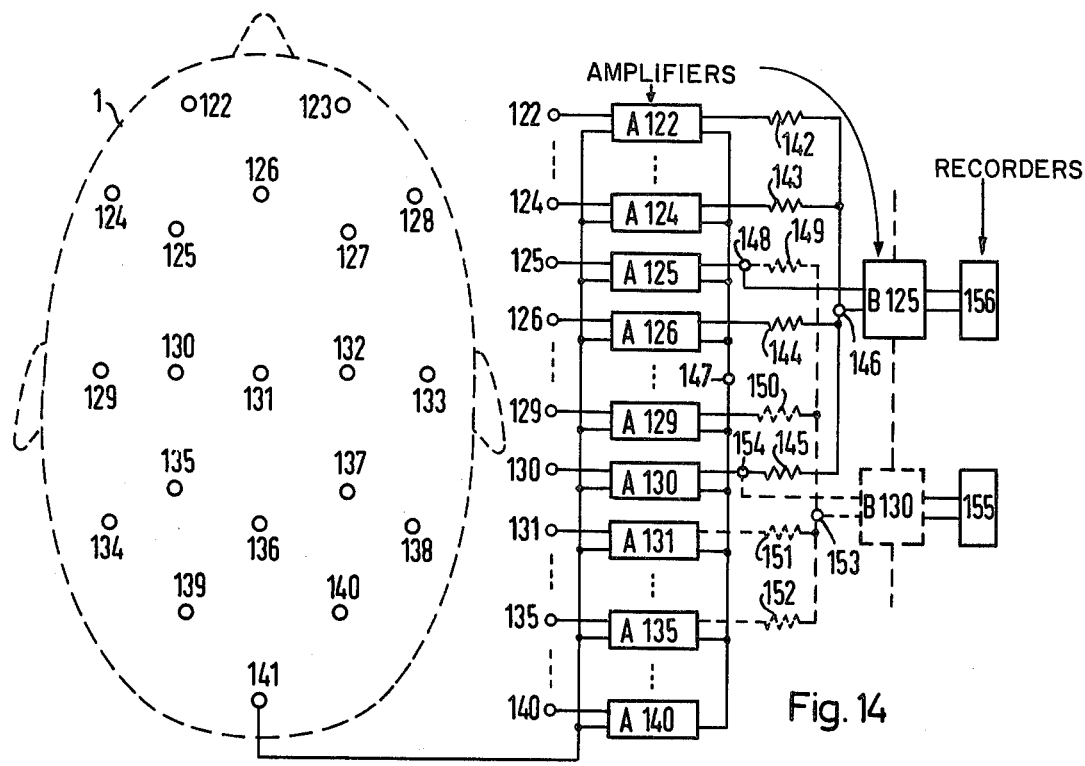
FIG. 14 shows a further circuit diagram illustrating the measuring method according to the present invention.

The measuring method according to the invention may also be used in an electrode arrangement according to FIG. 14 wherein a number of electrodes are placed on the skull 1 of a patient in a pattern according to an internationally established standard, for example in a so-called 10–20 system. Each signal electrode is used in this case as an auxiliary electrode for adjacent signal electrodes. The bias or difference voltages, which are characteristic of the present invention, are formed only after one or several steps of amplification, which avoids loading the electrodes with a great number of resistors.

Each signal electrode 122 to 140 is connected in each case to an input of a differential amplifier A122 to A140 having a high input and a low output impedance and two inputs and two respective outputs. The other inputs of differential amplifiers A122 to A140 are connected to a reference electrode 141 placed on skull 1 of the patient.

It is intended, by way of example, to measure the potential occurring locally under and within the proximity of signal electrode 125. This may involve the use of auxiliary electrodes 124, 122, 126 and 130 which form a polygon. The picked-up potentials of electrodes 122, 124, 125, 126 and 130 are supplied to one input of the associated amplifiers A122, A124, A125, A126 and A130. The corresponding outputs of amplifiers A122, A124, A126 and A130 are connected to a common point 146 by way of resistors 142 to 145. The potential under reference electrode 141 is supplied to the second inputs of said amplifiers. The second outputs of said amplifiers A122, A124, A125, A126 and A130, like the respective outputs of all amplifiers A122 to A140, are connected to a common point 147 (output point). The differential amplifier B125 measures the difference between the potential at output 148 of amplifier A125 and the potential at point 146 of the resistor network. The potential of said point 146 is the mean value of the output voltages of amplifiers A122, A124, A126, A130, because the outputs of all amplifiers A122 to A140 are lower ohmic outputs. The output voltage of differential amplifier B125 is supplied to an ink jet recorder 156 for recording purposes and this output voltage corresponds to the potential present under signal electrode 125 and within an area defined by auxiliary electrodes 122, 126, 130, 124.

The potentials under electrodes 122 to 141 are designated in the present case by $V_{122}$ to $V_{141}$. The amplification in amplifiers $A_{122}$ to $A_{140}$, for the sake of simplification, is assumed to be equal 1. The output voltage of amplifier $A_{122}$ is $V_{122} - V_{141}$. Between point 146 and output point 147, said voltage reduces to:

$$\frac{V_{122} - V_{141}}{4}$$

Between points 146 and 147, the output voltages are added by amplifiers A122, A124, A126 and A130 as follows:

$$\frac{V_{122} - V_{141}}{4} + \frac{V_{124} - V_{141}}{4} + \frac{V_{126} - V_{141}}{4} + \frac{V_{130} - V_{141}}{4}$$

The output voltage of amplifier A125 between points 148 and 147 is $V_{125} - V_{141}$. The differential amplifier B125 measures the voltage between points 148 and 146, i.e.:

$$V_{125} - V_{141} - \left( \frac{V_{122} - V_{141}}{4} + \frac{V_{124} - V_{141}}{4} + \frac{V_{126} - V_{141}}{4} + \frac{V_{130} - V_{141}}{4} \right)$$

which is equal to:

$$V_{125} - \frac{V_{122} + V_{124} + V_{126} + V_{130}}{4}$$

Therefore, the output voltage of differential amplifier B125 corresponds to the difference between the potential under signal electrode 125 and the mean value of the potentials of auxiliary electrodes 122, 126, 124 and 130.

The voltage under reference electrode 141 has been eliminated.

If the locally occurring potential is to be measured within the range of electrode 130, the adjacent electrodes 125, 129, 131 and 135 will be used as auxiliary electrodes. The potentials picked up from these electrodes are supplied to the inputs of the associated amplifiers A125, A129, A130, A131 and A135. The respective outputs of said amplifiers are connected to point 153 by way of resistors 149 to 152 shown by dash lines in FIG. 13. The voltage within the range of reference electrode 141 is supplied to the other inputs of amplifiers A125, A129, A130, A131 and A135. The corresponding outputs are in this case also combined at output point 147. Differential amplifier B130, shown in FIG. 13 in dash lines, picks up the difference between output 154 of amplifier A130 and point 153 of the resistor network. The output voltage of differential amplifier B130 is conducted to ink jet recording device 155. This voltage corresponds to the potential which occurs under signal electrode 130 and within the polygon formed by auxiliary electrodes 125, 129, 131 and 135. The locally occurring potentials are similarly picked up under the other electrodes.

The measuring method described above may be employed also in connection with the perimetral electrodes 122, 123, 128, 133, 138, 140, 139, 134, 129 and 124. The two adjacent perimetral electrodes are, in each case, used as auxiliary electrodes for each of said perimetral electrodes. For example, if electrode 129 is a signal electrode, electrodes 124 and 134 are used as the mean value-forming auxiliary electrodes. The differential amplifier associated with signal electrode 129 thus picks up the difference between the one output of amplifier A129 and the center point of the two resistors connected to the outputs of amplifiers A124 and A134.

As distinct from known measuring methods, it is possible in this way to achieve also for the perimetral electrodes superior exactness in determining the local electrode potential.

The measuring method described in the aforegoing and the arrangements for carrying out this method are also applicable to the measuring of other bioelectrical signals, for example, in connection with an electrocardiogram (EGG) of a fetus.

What is claimed is:

1. A method of measuring the bioelectrical activity occurring in the region under a signal electrode placed on a patient, wherein a plurality of auxiliary electrodes placed on the patient are used, said method comprising producing a mean potential value of the potentials of said auxiliary electrodes, forming a difference value between said mean potential value and the potential of said signal electrode, and supplying said difference value to a recording device, said auxiliary electrodes being exclusively electrodes disposed adjacent said signal electrode, and said auxiliary electrodes being arranged about the signal electrode to form a polygon if connected, with said signal electrode disposed in the center of said polygon.

2. A method of measuring the bioelectrical activity occurring in the region under a signal electrode placed on a patient, wherein a plurality of auxiliary electrodes placed on the patient are used, said method comprising producing a mean potential value of the potentials of said auxiliary electrodes, forming a difference value between said mean potential value and the potential of said signal electrode, and supplying said difference value to a recording device, said auxiliary electrodes being exclusively electrodes disposed adjacent said signal electrode, and at least one of said plurality of auxiliary electrodes being also operable as an adjacent signal electrode, whereby a plurality of signal electrodes comprising said first-mentioned signal electrode and said adjacent signal electrode are applied to the patient, said first-mentioned signal electrode being connected to contribute to a mean potential value for said adjacent signal electrode, thereby to perform a dual function.

3. Apparatus for measuring bioelectrical activity of a patient comprising a signal electrode adapted to be placed on a patient, a plurality of auxiliary electrodes adapted to be placed on the patient, adjacent said signal electrode, means connecting said auxiliary electrodes to provide a mean potential value thereof, difference determining means connected to determine the difference value between said mean potential value and the potential of said signal electrode, and recording means coupled to said difference determining means to record the difference value as indicative of the bioelectrical activity under and within the proximity of said signal electrode, said connecting means being connected only to auxiliary electrodes adjacent said signal electrode wherein said means connecting said auxiliary electrodes comprises resistors connected to respective auxiliary electrodes and to a neutral point, the magnitude of the resistance values of said resistors being respectively dependent on the spacing between each said auxiliary electrode and the signal electrode.

4. Apparatus for measuring bioelectrical activity of a patient comprising a signal electrode adapted to be placed on a patient, a plurality of auxiliary electrodes adapted to be placed on the patient, adjacent said signal electrode, means connecting said auxiliary electrodes to provide a means potential value thereof, difference determining means connected to determine the difference value between said mean potential value and the potential of said signal electrode, and recording means coupled to said difference determining means to record the difference value as indicative of the bioelectrical activity under and within the proximity of said signal electrode, said connecting means being connected only to auxiliary electrodes adjacent said signal electrode, an electrode-support device supporting said signal electrode and said auxiliary electrodes, said electrode-support device being made of insulating material, said signal electrode being centrally disposed in the electrode-support device and said auxiliary electrodes being peripherally disposed on said electrode-support device, said auxiliary electrodes forming a polygon if connected.

5. Apparatus for measuring bioelectrical activity of a patient comprising a signal electrode adapted to be placed on a patient, a plurality of auxiliary electrodes adapted to be placed on the patient, adjacent said signal electrode, means connecting said auxiliary electrodes to provide a mean potential value thereof, difference determining means connected to determine the difference value between said mean potential value and the potential of said signal electrode, and recording means coupled to said difference determining means to record the difference value as indicative of the bioelectrical activity under and within the proximity of said signal electrode, said connecting means being connected exclusively to auxiliary electrodes adjacent said signal electrode, at least one of said plurality of auxiliary electrodes being also operable as an adjacent signal electrode and having a plurality of further auxiliary electrodes disposed adjacent thereto but spaced relative to said first-mentioned signal electrode, thereby to provide a plurality of signal electrodes comprising said first-mentioned signal electrode and said adjacent signal electrode each having adjacent auxiliary electrodes and said first-mentioned signal electrode also functioning as one of the auxiliary electrodes for said adjacent signal electrode, said mean potential value providing means comprising a plurality of first differential amplifiers having a high input and a low output impedance and two inputs and two corresponding outputs; each electrode being connected to one input of a respective first differential amplifier, a reference electrode adapted to be placed on a patient, the other inputs of said first differential amplifiers being commonly connected to said reference electrode, the outputs of said first differential amplifiers corresponding to said reference electrode being connected to a common output point, said difference determining means comprising an output differential amplifier for each signal electrode, and said mean potential value providing means further comprising resistor networks including resistors connected to the electrode outputs of those first differential amplifiers corresponding to the electrodes which are disposed adjacent the signal electrode at which the voltage is to be measured, said resistors being connected to a common neutral point for receiving said mean potential value, one input of said output differential amplifier being connected to the signal electrode output of the associated first differential amplifier and the other input of said output differential amplifier being connected to the neutral point of said resistor network.

* * * * *